United States Patent [19]

Edwards

[11] Patent Number: 5,201,856
[45] Date of Patent: Apr. 13, 1993

[54] EYEGLASSES AND RETAINER THEREFOR INCLUDING EAR PROTECTOR

[75] Inventor: Michael D. Edwards, Hood River, Oreg.

[73] Assignee: Shred Alert Products, Inc., Hood River, Oreg.

[21] Appl. No.: 766,891

[22] Filed: Sep. 24, 1991

Related U.S. Application Data

[63] Continuation of Ser. No. 487,783, Mar. 5, 1990, abandoned.

[51] Int. Cl.⁵ .......................... A42B 1/06; G02C 3/02
[52] U.S. Cl. ...................................... 2/209; 351/123; 351/156
[58] Field of Search .................. 2/13, 209, 203, 449; 351/156, 157, 155, 123, 122

[56] References Cited

U.S. PATENT DOCUMENTS

| | | | |
|---|---|---|---|
| D. 207,187 | 3/1967 | Gould | 351/156 X |
| 3,173,147 | 3/1965 | Gross et al. | 351/156 X |
| 4,133,604 | 1/1979 | Fuller | 351/123 |
| 4,751,746 | 6/1988 | Rustin | 2/13 |
| 4,790,646 | 12/1988 | Seron | 351/156 |
| 4,818,094 | 4/1989 | Lyons | 351/157 |

*Primary Examiner*—Peter Nerbun
*Attorney, Agent, or Firm*—Robert L. Harrington

[57] ABSTRACT

An article of wearing apparel that is configured to be worn by an individual as an ear protector and eye glasses retainer. The article is adjustably attachable to a pair of glasses by utilizing formed sleeves that receive the bows of the glasses. Each of the sleeves grips the bows as with an elastomeric material forming a part of the sleeve that clings to the bows of the glasses. The article worn on the head of the individual covers the ears to provide protection and being attached to the glasses, retains the glasses in position.

3 Claims, 2 Drawing Sheets

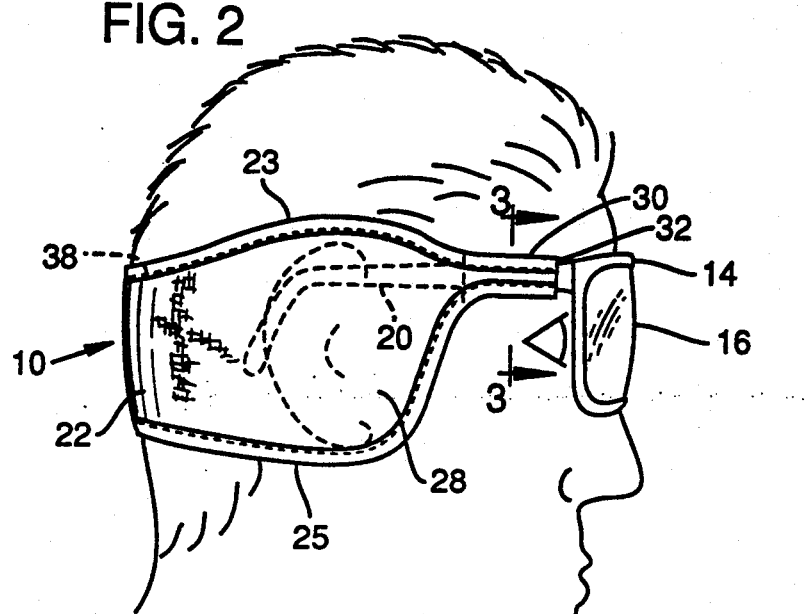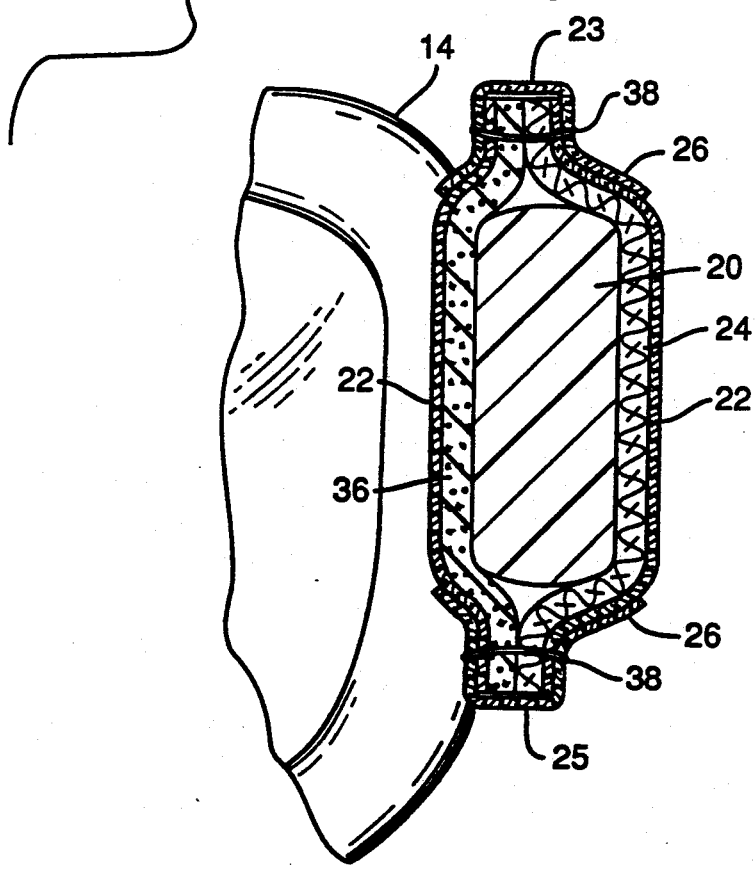

EYEGLASSES AND RETAINER THEREFOR INCLUDING EAR PROTECTOR

This is a continuation of co-pending application Ser. No. 487,783 filed on Mar. 5, 1990, now abandoned.

BACKGROUND INFORMATION

1. Field of the Invention

This invention relates to protective wearing apparel and in particular it relates to a combination ear protector and eye glasses retainer.

2. Background of the Invention

Participants in outdoor activities such as skiing desire protection for their eyes and ears. Protective glasses, whether they are prescription to correct a visual defect or just plain glasses, are worn to shield the eyes from wind and to prevent air borne particles such as dirt, snow or rain from getting into their eyes. Glasses of either type may also be tinted to reduce glare from snow or light colored surfaces. Since the ears have a large surface area exposed to the elements it is generally desirable to have them covered for protection, especially from the cold.

There are many devices that are designed to provide eye protection, be it from glare, dust or other irritants. Likewise, there are ear bands, muffs and the like on the market to provide a covering for the ears. Insofar as known, however, there has not been a product on the market that will satisfactorily provide protection for both the eyes and ears of a participant in an outdoor activity such as skiing. The eye glasses of an active outdoor individual often will not stay in place or they will fall off completely, just from the jostling activity of the individual. Elastic bands are sometimes fastened to each end of the bows of the wearer's eye glasses and extended around the back of the head. These however, generally place undesired tension on the glasses and do not protect the wearer's ears.

Numerous patents have issued covering various forms of ear protectors and eye glasses retainers. Included are U.S. Pat. No. 4,751,746 issued to Rustin, U.S. Pat. No. 4,520,510 and U.S. Pat. No. 4,712,254 issued to Daigle, U.S. Pat. No. 3,173,147 issued to Gross, et al, U.S. Pat. No. 4,616,367 issued to Jean, et al, U.S. Pat. No. 4,682,374 issued to Geiser and U.S. Pat. No. 4,670,911 issued to Dunford.

None of these numerous variations achieve applicant's objective of providing a head band configured to protect the wearer's ears and which attaches to conventional eye glasses for cooperatively retaining the ear protecting band and eye glasses on the wearer who engages in physical activity.

SUMMARY OF THE INVENTION

The present invention is a combination ear protector and eye glasses retainer that provides protection for the ears and retains the eye glasses in their proper position. The combination ear protector and eye glasses retainer of the present invention is highly functional, appealing to the user, and readily adapted to the user's standard eye glasses.

The ear protector and eye glasses retainer of the preferred embodiment has tubular sleeves into which the bows of the glasses are inserted. An adhering material is incorporated in the sleeves that clings to and grips the bows of the glasses. The sleeves are moveable along the bows for adjustment purposes. The ear protector and eye glasses retainer is constructed so that the ear protector extends around the back of the head of a user with a shaped portion covering each ear. It is attached to the eye glasses as explained and retains them in position.

BRIEF DESCRIPTION OF THE DRAWINGS

FIG. 2 is a side view of an individual wearing the ear protector and eye glasses retainer of FIG. 1;

FIG. 3 is an enlarged sectional view of the bow gripping sleeve and bow taken on view line 3—3 of FIG. 2;

DESCRIPTION OF THE PREFERRED EMBODIMENT

Figure 1:
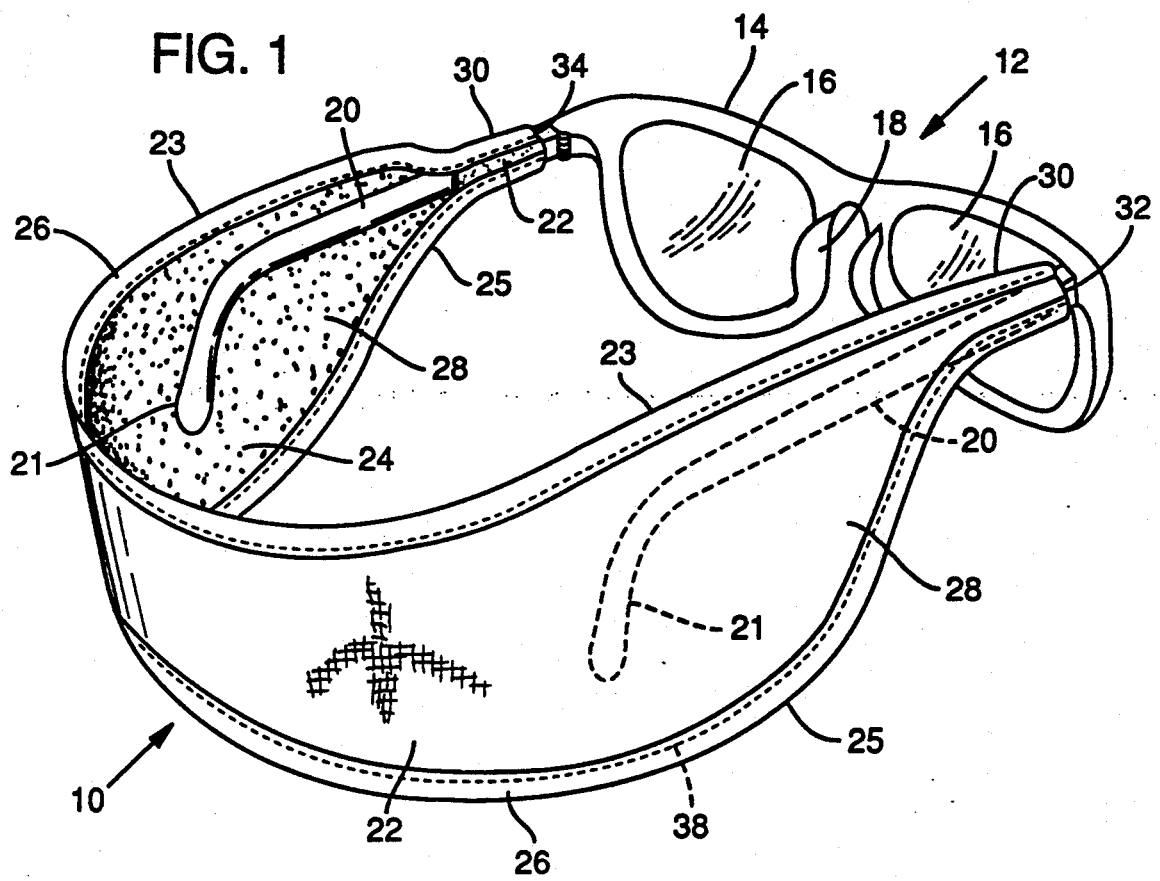
FIG. 1 is a perspective view of an ear protector and eye glasses retainer in accordance with the present invention.

Refer now to FIGS. 1 and 2 of the drawings. FIG. 1 shows, in perspective view, the shaped ear protector and eye glasses retainer, hereafter referred to as the protector 10, installed on a pair of eye glasses 12. FIG. 2 shows more clearly, the shaped configuration of the protector 10 when worn by a user.

The pair of glasses 12, typical of those on the market, has a frame 14 into which lenses 16 are mounted, a nosepiece 18 on the frame 14 between the lenses 16 and a pair of shaped bows (temple pieces) 20. One end of each bow 20 is mounted on the frame 14 in a hinged arrangement and an end 21 of the bows 20 has a configured section to fit over the ear of the individual.

The protector 10 as shown in FIG. 1 is installed on the bows 100 of the glasses 12. The shaped protector 10 is of layered construction, each layer composed of a pliable cloth-like material, either natural or man-made. The layered construction includes an outer layer 22 that is preferably of water resistant material, and an inner layer 24 that is preferably of insulating type material. As shown in FIG. 1, the protector has an upper edge 23 (border), a lower edge 25 (border) and ends 32 and 34, with the upper and lower edges 23, 25 converging toward each other near each of the ends 32 and 34.

A formed sleeve 30, which will later be described in more detail, is provided at the convergence of the upper and lower edges 23, 25, at each of the ends 32 and 34. The upper edge of the outer layer 22 and the inner layer 24 are adjoined by fitting the upper edges of the layers 22 and 24 between the folds of a folded band or border 26 and securing the layers 22 and 24 between the folds of the folded border 26 as by sewing. The lower edges of the layers 22 and 24 are adjoined by another folded border 26 in the same manner. It is preferable to utilize the gathering technique in the sewing procedure so that the protector is formed into a pocket-like area, i.e. it is cupped as indicated generally at 28 to thereby envelop the ears of the wearer. As shown in FIG. 2, each of the cupped areas 28 is sufficiently large to cover the ear of the individual, and dimensionally large enough to permit the protector 10 to cover the ear without forcing the ear toward the head in an uncomfortable manner. The cupped or formed pocket area 28 of the protector 10 while covering the ear permits the bands 26 of the protector 10 to be in contact with the head and face of the individual to provide a seal against the elements.

As shown in FIGS. 1-3, the protector 10 is slidably installed on the bows 20 of the glasses 12 with the sleeve 30 at end 34 fitting over (encircling) a portion of one, of the bows 20 and the sleeve 30 at end 32 fitting over (encircling) a portion of the other bow 20. To install, the end 21 of one of the bows 20 is inserted in the sleeve 30 at end 34 and the, end 21 of the other bow 20 is inserted into the sleeve 30 at end 32. The bows are slid through the sleeves 30 until they are at the desired position on the bows 20, with the ends 21 of the bows 20 in the vicinity of the pocket areas 28.

The tubular sleeves 30 are illustrated in detail in FIG. 3. The sleeves 30 are constructed as by sewing and as shown in the sectional view of FIG. 3, the sleeves 30 surround the bow 20 of the glasses 12. The right side of the sleeve 30, as viewed in the figure is formed by the layered construction of the outer layer 22 and the inner layer 24. The left side of the sleeve 30, as viewed in the figure, is constructed of an outer layer 22 (or in the alternative the outer layer may be of the same material as the inner layer 24) and an inner pad or sleeve section 36. The pad 36 is a material that has a "clinging" capability, that is it has a high adhering attribute and is preferably of a soft elastomeric or rubber-like material. As stated hereinabove, in the Background of the Invention section, elastic bands fastened to the bows of eyeglasses in the prior art generally place undesired tension on the eyeglasses. Applicant's elastomeric pad 36, in the FIG. 3 embodiment, differs from this prior art in that it extends only on one side of the sleeve, as previously stated in this paragraph. This structure as just described for the FIG. 3 embodiment would inherently avoid the abovementioned undesired tension on the eyeglasses. As shown in the figure, the pad 36 is in frictional contact with the bow 20 of the glasses 12. The top and the bottom of the sleeve 30 as viewed in FIG. 3 are individually constructed by folding the border 26 over and capturing the edges of the layers of the sleeve (i.e. the outer layer 22, inner layer 24, pad 36 and another outer layer 22) between the folds of the border 26 and fixedly securing each assembly into a unit as by sewing with stitches 38.

A preferred embodiment of the invention has been detailed and to those skilled in the art, many variations and modifications will be apparent without deviating from the true scope of the invention. A particular feature of the invention is the attachability of the protector to the bows of a conventional pair of eye glasses. Fastening means other than that disclosed may be developed without departing from the invention. Other variations will also be apparent. For example, it is readily apparent that the protector may be constructed of a single layer of material, the shape of the protector may be varied, the construction of the sleeve may vary and other features added or deleted for aesthetic appeal.

Figure 4:
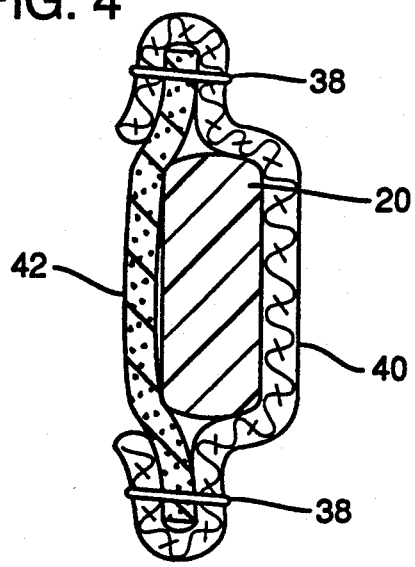
FIG. 4 is a view similar to FIG. 3 illustrating an alternate embodiment of the invention.
Figure 5:
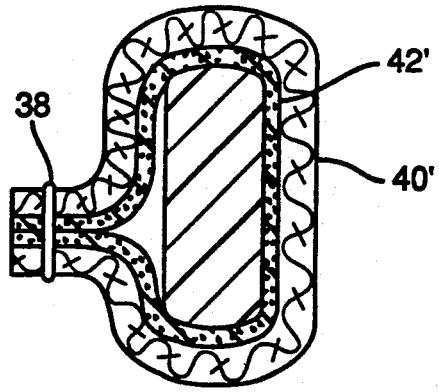
FIG. 5 is a view similar to FIG. 3 illustrating a second alternate embodiment.

FIGS. 4 and 5 illustrate two such alternate embodiments as concerns the provision of the gripping sleeve portions 32 and 34. In FIG. 4, a single layer of material 40 is folded over a rubber pad of material 42 and stitched with stitches 38. In FIG. 5 a single layer of material 40' is lined with the rubber material 42' and stitched with stitches 38. A third and alternate embodiment 25 would be one like FIG. 5 but without the rubber liner 42'.

It is believed that the versions of FIGS. 3 and 4 are better in providing a partial gripping surface of the rubber material, i.e. against the inside only of the bows 20. While wearing the protector, the bows are urged against the rubber surface and slipping is resisted. Yet the bow can be easily removed from the sleeve by manually pinching and then pulling the inside of the sleeve away from the bow and sliding the bow against the less adhering cloth material. In the version of FIG. 5, the bow will be more difficult to remove from the fully encased rubber sleeve and in the non-lined version, slipping during wearing is more likely.

The scope of the invention is therefore not limited to the disclosure as detailed by the drawings and written description, but is to be determined by the appended claims.

What is claimed is:

1. A combination eye glasses and retainer therefor worn by a user comprising:

a conventional pair of eyeglasses including a frame having a nose piece engaging the user's nose and a pair of bows extended rearwardly from the sides of the frame along the temples of the user's head and overlying the user's ears;

an elongated retainer of cloth-like material having opposed ends attached by adjustable attachment means to the eyeglasses' bows at the user's temples;

said attachment means provided by the retainer ends being configured into sleeves that surround the eyeglasses' bows, said sleeves each comprising a combination of materials including a layer of cloth-like material which is secured to a separate elastomeric pad, said layer of cloth-like material extending directly adjacent one side of each respective eyeglass bow, and said separate elastomeric pad extending directly adjacent an opposite side of each respective eyeglass bow for gripping the eyeglasses' bows to resist sliding of the eyeglasses bows through the sleeves, said combination of materials as provided in said sleeves having the property of permitting user adjustment and placement of the retainer ends at the desired position along said bows to enable the user to customfit the combination of the eyeglasses and retainer to the user's head and thereby avoid undesired tension on the eyeglasses, said retainer further including shaped portions rearwardly of said sleeve end portions shaped to cover the user's ears.

2. An article as defined in claim 1 wherein the retainer of cloth-like material comprises a laminate of two cloth layers including an outside layer and an inside layer, said outside layer being water repellent and said inside layer being a heat insulator.

3. An article as defined in claim 1 wherein the retainer is outline by stitching, said stitching gathering the material of the retainer in the area of the shaped portions to form pockets for the wearer's ears.

* * * * *